(12) United States Patent
Parnes

(10) Patent No.: US 6,302,109 B1
(45) Date of Patent: Oct. 16, 2001

(54) EVACUATING SURGICAL DRAPE SUPPORT

(76) Inventor: Robert E. Parnes, 6107 Kentucky Ave., Pittsburgh, PA (US) 15206

( * ) Notice: Subject to any disclaimer, the term of this patent is extended or adjusted under 35 U.S.C. 154(b) by 0 days.

(21) Appl. No.: 09/496,498

(22) Filed: Feb. 2, 2000

(51) Int. Cl.$^7$ .................................................. A61G 15/00
(52) U.S. Cl. ........................ 128/845; 128/847; 128/848
(58) Field of Search .................................. 128/845, 846, 128/847, 857, 858, 849–856, 202.18

(56) References Cited

U.S. PATENT DOCUMENTS

| | | |
|---|---|---|
| D. 318,920 | 8/1991 | Bruhl, Jr. . |
| 3,347,544 | * 10/1967 | Uffenorde ............................. 128/847 |
| 3,859,993 | * 1/1975 | Bitner .................................... 128/847 |
| 4,122,848 | * 10/1978 | Carpel .................................. 128/847 |
| 4,465,066 | 8/1984 | Carpel . |
| 4,699,131 | 10/1987 | Crook et al. . |
| 4,739,753 | 4/1988 | Brehm . |
| 5,140,997 | 8/1992 | Glassman . |
| 5,220,915 | 6/1993 | Troy et al. . |
| 5,488,944 | 2/1996 | Kennedy . |
| 5,730,153 | * 3/1998 | Cheng .................................... 128/847 |

OTHER PUBLICATIONS

David W. Eisle, M.D., "Complications in Head and Neck Surgery," Mosby (St. Louis, MO ), p. 316, (1993).

* cited by examiner

*Primary Examiner*—Michael A. Brown
(74) *Attorney, Agent, or Firm*—Thorp Reed & Armstrong

(57) ABSTRACT

The present invention provides a surgical drape support useful in head, neck or ophthalmic surgery, which supports the drape above and off the patient's face while actively removing exhaled air thus reducing carbon dioxide, heat and moisture levels from the space surrounding the patient's head and face. This device provides greater comfort to the patient during surgery by actively reducing the likelihood of claustrophobia from face-drape contact, reducing heat and moisture, and decreasing the risk of hypercarbia by removing exhaled air. The drape support additionally may reduce the risk of intra-operative fire under the surgical drapes resulting from a build up of supplemental oxygen under the drapes.

32 Claims, 5 Drawing Sheets

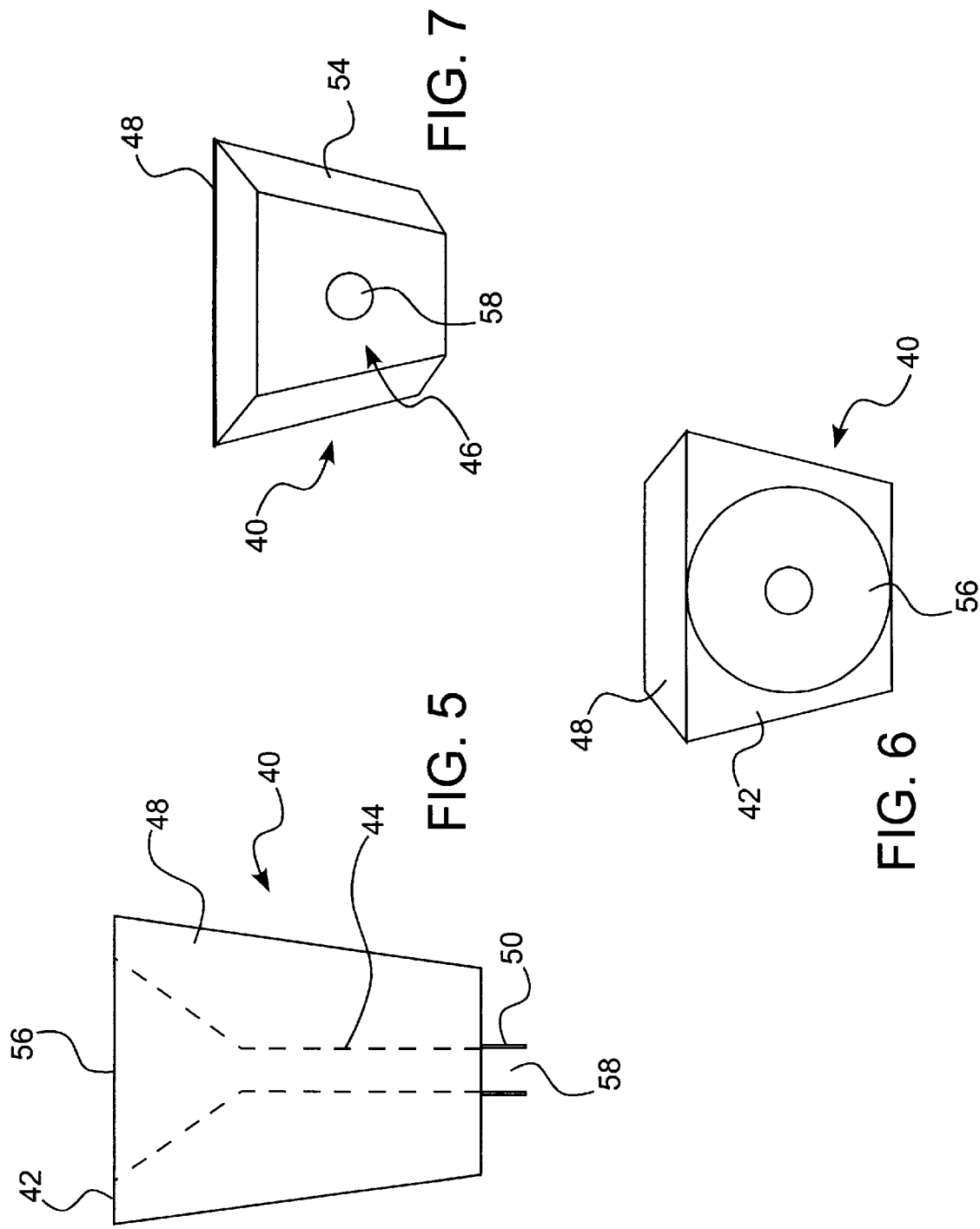

EVACUATING SURGICAL DRAPE SUPPORT

FIELD OF INVENTION

The present invention relates in general to the field of surgical drapes for head and neck surgery, and more specifically to an apparatus which supports a surgical drape over a patient's face during ophthalmic surgery.

BACKGROUND OF THE INVENTION

During ophthalmic and Head and Neck surgery, a sterile surgical field is required to prevent infection. In ophthalmic surgery, the patient's entire head and body are covered by the sterile drapes. These drapes are usually composed of a combination of cotton or synthetic fabric combined with plastic. The plastic drape usually covers the patient's entire face (example 3-M Corporation 10–60 drape). Other drapes cover the entire head and face with synthetic fiber cloth with plastic covering only the operated eye. Both types of drapes cover the entire face. The drapes are form-fitting and are applied around the operated eye with adhesive. This causes the drape to come in contact with the patient's face nearly 100% of the time.

More than 95% of ophthalmic surgical procedures are performed under local anesthesia. The patient is given topical or injectable anesthesia around the eye. The patient is rarely put to sleep with general endotracheal intubation. Many patients are given intravenous medications for sedation and comfort. Patients who are awake during their surgery may experience feelings of claustrophobia from lying under the plastic drapes closely adherent to the eye, nose and mouth. In addition, the exhalation under a form fitting plastic drape can make a patient feel warm, sweaty and uncomfortable. As the perspiration and temperature rises, it can make the patient feel anxious, contributing to a further sense of claustrophobia and panic.

Carbon dioxide ($CO_2$) is a prominent component of exhaled air. When a patient is under sterile drapes during surgery, exhaled air and supplemental oxygen can be trapped under form-fitting drapes. As a result, it is possible that both $CO_2$ and oxygen levels may rise as air is trapped under the form-fitted drapes. Patients are usually given supplemental oxygen through a nasal cannula or mask under the drapes. This helps to prevent hypoxia (low oxygen blood levels). It does not, however, prevent the slow build up of carbon dioxide under the drape, which can lead to hypercarbia.

Hypercarbia is a potentially dangerous condition that occurs when carbon dioxide levels rise in the blood stream. It can occur from breathing higher levels of carbon dioxide. A person suffering from early hypercarbia may respond in an agitated or combative manner. This is a major concern during long and delicate procedures. Ophthalmic surgical procedures performed under local anesthesia necessitate the patient to lay still for upwards of two hours or more. A patient can easily become agitated during the surgery if he becomes claustrophobic or uncomfortably warm or sweaty as a result of exhaled air trapped under the drape. If carbon dioxide levels rise, leading to hypercarbia, this can make a borderline situation worse. An agitated patient may require deeper sedation to keep him calm. This additional anesthesia, in some cases, may provide the effect opposite than that intended by increasing and exacerbating hypercarbia. Even if it does not worsen the hypercarbia, the extra sedation can increase the risks to the patient and increase the amount of time that the patient spends recovering from the effects of anesthesia.

Form-fitting surgical drapes used in head, neck and ophthalmic surgery tend to increase a patient's discomfort and increase levels of anxiety and claustrophobia. These surgical drapes also allow exhaled air and supplemental oxygen to be trapped under the drapes. This facilitates an increase in temperature, humidity and perspiration under the drapes and contributes to both rising oxygen and $CO_2$ levels. A number of prior art devices have attempted to address these problems with varying degrees of success.

DESCRIPTION OF THE PRIOR ART

One solution to the above-described problems encountered with surgical drapes is to provide a support to lift the surgical drape off the patient's face. A number of drape support devices have been patented. These devices do not resolve the problems encountered in head and neck surgery in general and ophthalmic surgery in particular.

U.S. Pat. No. 4,122,848 issued to Carpel describes an apparatus, the base of which is attached to the patient's nose with adhesive tape. The base has a loop structure attached to it to elevate the surgical drape away from the patient's nose and mouth area. This invention has several drawbacks. First, it requires the use of a surgical implement table, positioned above the patient's chest, to help support the drape. Second, the invention provides for only passive escape of accumulated $CO_2$ from around the edges of the drape and appears unlikely to remove heat and moisture. Third, because this invention must be used in conjunction with a surgical implement table, it is likely to impede the surgeon's access to the area around the patient's face.

U.S. Pat. No. 4,465,066, also issued to Carpel, describes a T-shaped device, made of cardboard, in which one leg of the "T" is attached to a patient's right check and the other to his left check, with the third leg of the "T" being attached to the bridge of the patient's nose. This invention also requires an implement table suspended over the patient's chest to help support the drape. This device allows the surgeon slightly more access to the area around the patient's face, but still only provides for passive removal of accumulated $CO_2$ by allowing it to escape from around the edges of the drape, and provides for no removal of heat and moisture. Another disadvantage of this invention lies in the fact that because of its cardboard construction, it may weaken and allow the drape to come much closer to the face than originally intended, thereby increasing the likelihood of claustrophobic reactions, heat and moisture build-up, and hypercarbia. Another disadvantage of this invention is that the legs of the T-shaped member are attached to the patient's face by an adhesive disk. Attachment to the patient by adhesive is prone to loosening and/or detaching as a result of the patient's perspiration and/or movements of the patient's facial muscles.

U.S. Pat. No. 4,699,131 issued to Crook et al. describes a mask-like device which is designed to fit over the patient's nose and mouth. The W-shaped member of the mask raises the drape above the patient's mouth, thereby preventing the drape from contacting the face. Front and back legs are attached to the device, thus eliminating the problems encountered in taping a device to a patient's face. Several disadvantages are noted with the use of this device. This device, like the other above-mentioned devices, provides for passive escape of accumulated $CO_2$ from around the edges of the surgical drape and no removal of heat or moisture. The W-shaped member protruding above the patient's mouth can interfere with placement of surgical equipment, such as a microscope, which may be necessary for eye surgery, over the patient. The bulky nature of this invention may also restrict the surgeon's access to the area around the patient's face. Finally, the W-shaped member may not keep the drape sufficiently far from the patient's face to prevent heat and moisture build-up, claustrophobia and/or hypercarbia.

A surgical drape support which facilitates the delivery of oxygen or anesthetic gas to a patient is described in U.S. Pat. No. 4,739,753 granted to Brehm. A flexible conduit is fitted onto a one leg of bracket that supports the conduit above the patient. The other leg of the L-shaped bracket is placed beneath the patient. The adjustable conduit connects to a nozzle that can support a surgical drape above the patient's face. An air supply tube is threaded through the conduit and attached to the nozzle, thereby providing oxygen or anesthetic gas to the patient. Disadvantages of this device are that it to provides only for passive evacuation of $CO_2$ from around the edges of the surgical drape with no provision for removal of heat and moisture. Also, the conduit suspended above the patient may tend to sag over time, thereby increasing the patient's claustrophobic feelings. The suspended conduit and nozzle structure may also restrict the surgeon's access to the area around the patient's face.

U.S. Pat. No. 5,140,997 issued to Glassman describes a surgical drape for ophthalmic surgery that contains eye holes and is designed to fit tightly over the patient's face. The drape also has a piece of tubing incorporated into it for providing oxygen to the patient. An opening in the drape, which is meant to cover the mouth, contains filtering material, that allows the patient to exhale, but prevents bacteria, fluids or other particulate matter from escaping. This invention reduces the restriction of the surgeon's access to the area around the patient's face, but it is not likely to reduce the risk of hypercarbia, heat and moisture build-up and/or claustrophobic sensations. In fact, because of its tight fit on the patient, this invention may serve to increase patient anxiety and discomfort.

U.S. Pat. No. 5,220,915 issued to Troy et al. describes an air delivery device, which is suspended above a patient's chest by a pair of legs that slide under the patient. The device also elevates the surgical drape over the patient's face. The device is situated about the patient's chest area and provides a jet of air across the patient's face during surgery. The disadvantage of this invention is that the drape may sag onto the patient's face during surgery, thereby causing claustrophobic sensations, heat and moisture build-up and possibly, hypercarbia because in the device, like the other devices mentioned above, $CO_2$ removal is passive.

U.S. Pat. No. 5,488,944 granted to Kennedy describes a device consisting of a flexible, plastic strip with adhesive media on the ends thereof. The device is attached to the patient's face via this adhesive media. The device has a tube for providing oxygen along with a tube for sampling $CO_2$ levels. A disadvantage of this device is that the adhesive may loosen due to patient perspiration and/or facial movements, thereby weakening the drape support and allowing the surgical drape to contact the patient's face. The device provides for only passive evacuation of accumulated $CO_2$ from around the edges of the drape with no provisions for the removal of heat and moisture. The hoses contained in the device may tend to weigh it down, possibly causing the drape to contact the patient's face. Also, the hoses can accidentally become entangled with operating room personnel, thereby causing the support to flatten and resulting in the drape contacting the patient's face with resultant claustrophobia, heat and moisture build-up and possible hypercarbia.

A few eye surgeons have used an unpatented device that consists essentially of an empty bottle commonly found in operating rooms and some tubing. The bottle, attached to the patient's sternal region by adhesive tape, lifts the drape above the face. The bottle's cap may be removed and a hole can be cut in the bottle's bottom to allow for insertion of a suction line, commonly found in operating theaters, so that this device can be used to actively remove the $CO_2$, heat and moisture from around the patient's face. This device is superior to the above-mentioned devices, but it possesses some drawbacks. First, because the device consists of a rounded object, the bottle, placed on a flattened surface, the patient's chest, the apparatus may roll off the patient during the surgery. Second, the device must be taped to the patient, thereby using an inherently unreliable method which is susceptible to loosening from perspiration and/or patient body movements. Finally, the bottle, because of its shape and size, may interfere with the surgeon's ability to use equipment, such as a microscope, during surgery.

Specifically, the above-detailed devices do not:
1) combine to raise drapes above the patient's face in a manner that does not encumber the surgeon due to the size, location (or both) of the supports;
2) provide for the active removal of exhaled air, which would allow temperature, humidity, and $CO_2$ levels to be optimized in order to prevent complications as described above;
3) allow for the simultaneous use of a nasal cannula or a face mask to provide supplemental oxygen to the patient while providing an active method to remove excess oxygen in an attempt to minimize the risks of fire under operating room drapes as noted in "Complications of head and Neck Surgery", Chapter 37, Mosby Publisher, St. Louis, Mo. 1993;
4) provide a disposable, economical, single-patient-use device to accomplish the previously mentioned objectives without the risk of passing air-borne infections to other patients; and
5) allow surgical technicians and assistants unencumbered access to established necessary equipment within the surgical field.

Therefore, a need exists in the art for a device useful in head and neck surgery in general, and in ophthalmic surgery in particular which would minimize or perhaps eliminate the problems discussed above. It should be effective, easy to use, economical and disposable. Such a device should provide the patient with greater comfort during surgical procedures and decrease claustrophobic feelings, heat and moisture build up and decrease the likelihood of hypercarbia, while providing support for the surgical drape.

SUMMARY OF THE PRESENT INVENTION

The preferred embodiment of the present invention provides a surgical drape support for head, neck and ophthalmic surgery, comprising a member having trapezoidal top, bottom, front and rear faces with a first and second side face. The present invention provides a drape support which will raise the surgical drape above the patient's face with minimal restrictions on the surgeon's access to the area around the patient's face. The preferred embodiment of the drape support of the present invention also provides a funnel-shaped passageway through the drape support for the active removal of $CO_2$, heat and moisture from the space around the patient's face under the drape. Such a device should provide the patient with greater comfort during surgical procedures and decrease claustrophobic feelings, heat and moisture build-up and the likelihood of hypercarbia, while providing support for the surgical drape.

BRIEF DESCRIPTIONS OF THE DRAWINGS

The present invention will now be described for purposes of illustration and not limitation in conjunction with the following figures, wherein:

FIG. 5 is a top view of an embodiment of the present invention;

FIG. 6 is a front view of an embodiment of the present invention; and

FIG. 7 is a rear view of an embodiment of the present invention.

DETAILED DESCRIPTION OF THE INVENTION

Figure 1:
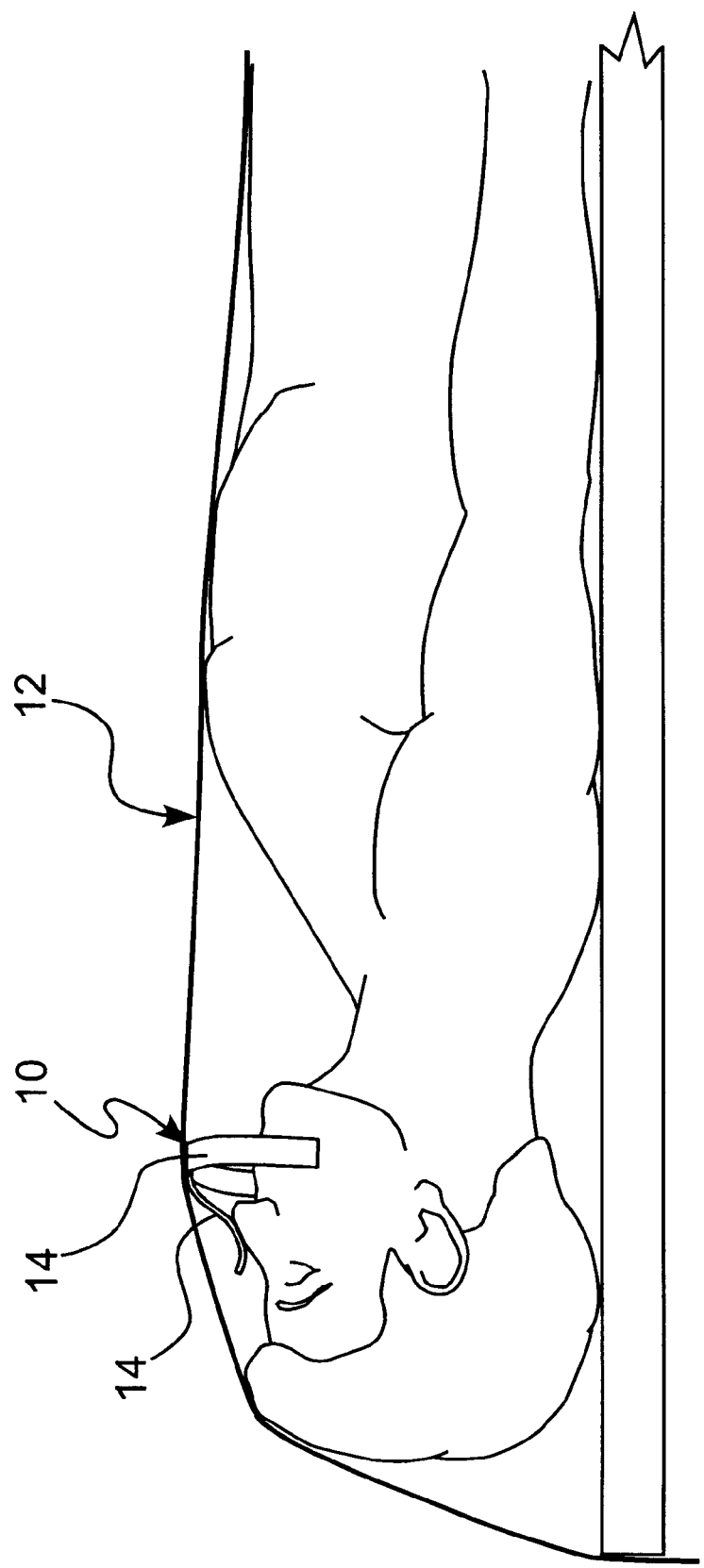
FIG. 1 is a depiction of a prior art "T"-shaped plastic strip device.

FIG. 1 illustrates a prior art "T"-shaped device 10 for supporting a surgical drape 12 above a patient. The legs 14 of the "T" are attached to the patient's cheeks and bridge of the nose via adhesive material.

Figure 2:
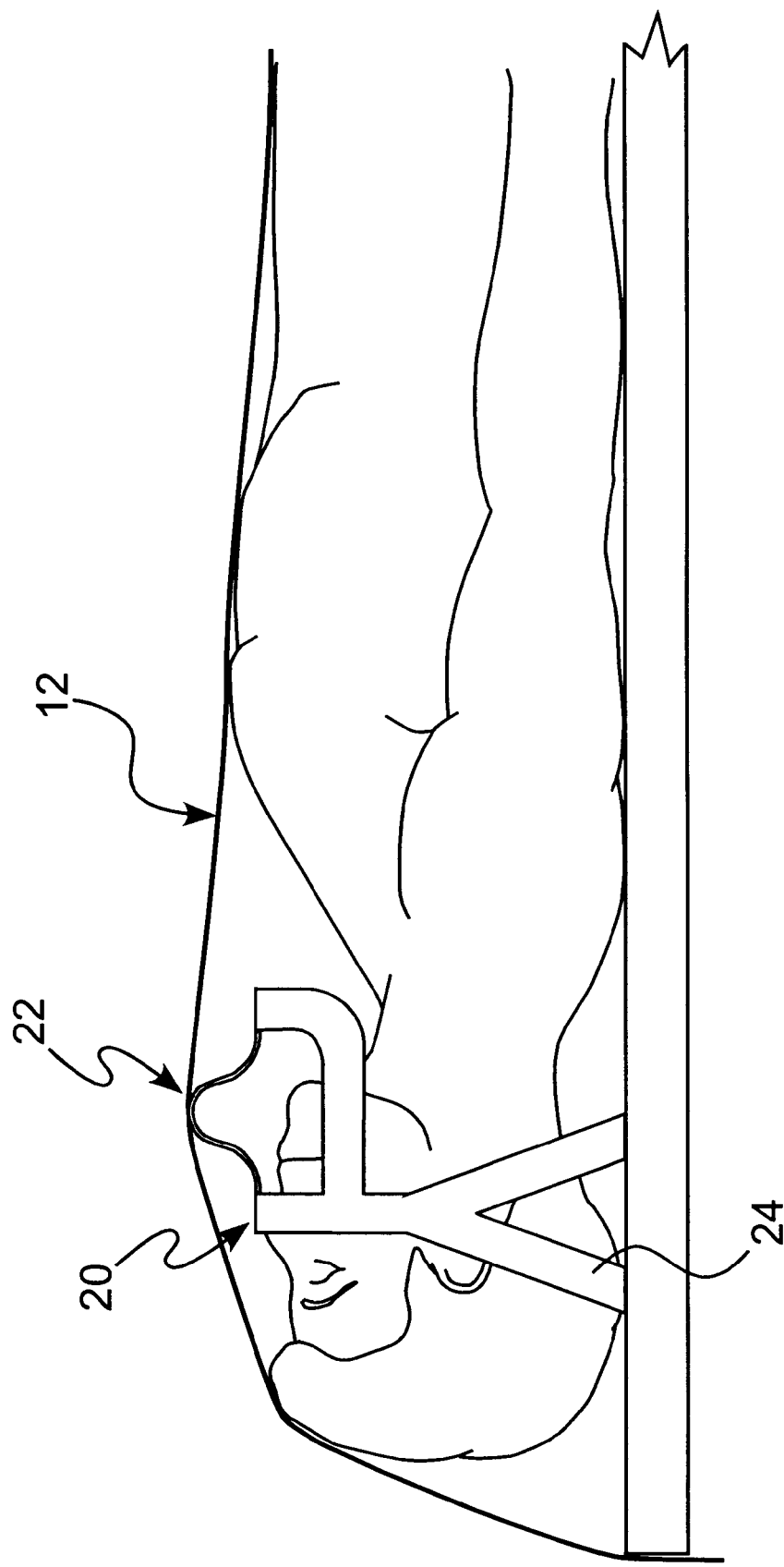
FIG. 2 is a depiction of a prior art face mask device.

FIG. 2 depicts a prior art mask-type device 20. The surgical drape 12 is supported above the patient's face by a member 22 of the mask 20. Legs 24 support the mask above the patient's face.

Figure 3:
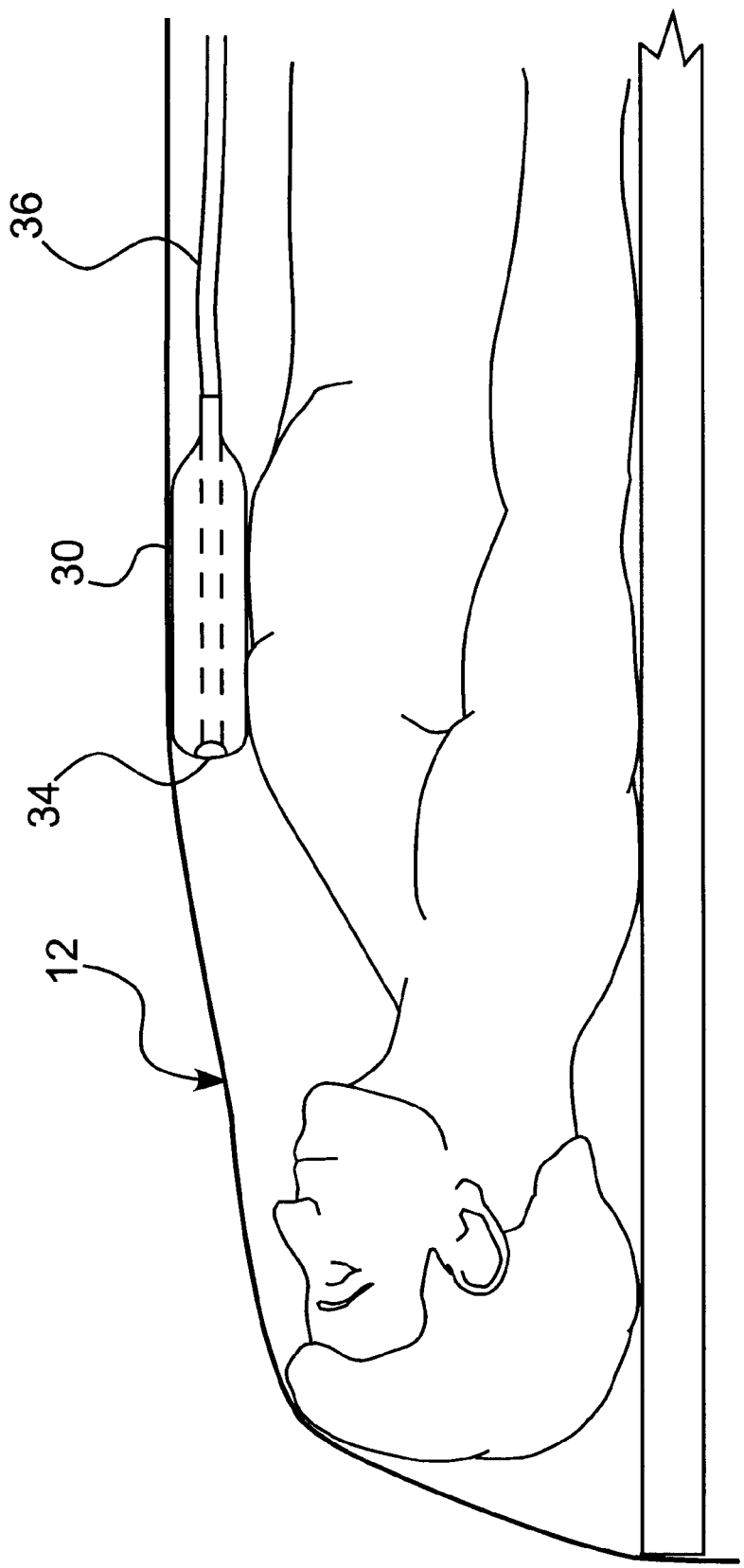
FIG. 3 is an illustration of an unpatented prior art device utilizing an empty plastic bottle.

An unpatented device used by a few eye surgeons is shown in FIG. 3. The surgical drape 12 is supported by an empty bottle 30. A hole 34 may be cut into the bottle's bottom and a suction line 36 can be inserted to evacuate exhaled air.

FIGS. 4 through 7 depict a preferred embodiment of the present invention. The depicted preferred embodiment supports the surgical drape 12 above the patient's face, capable of actively removing exhaled air containing heat, moisture and carbon dioxide from the air space under the surgical drape.

Figure 4:
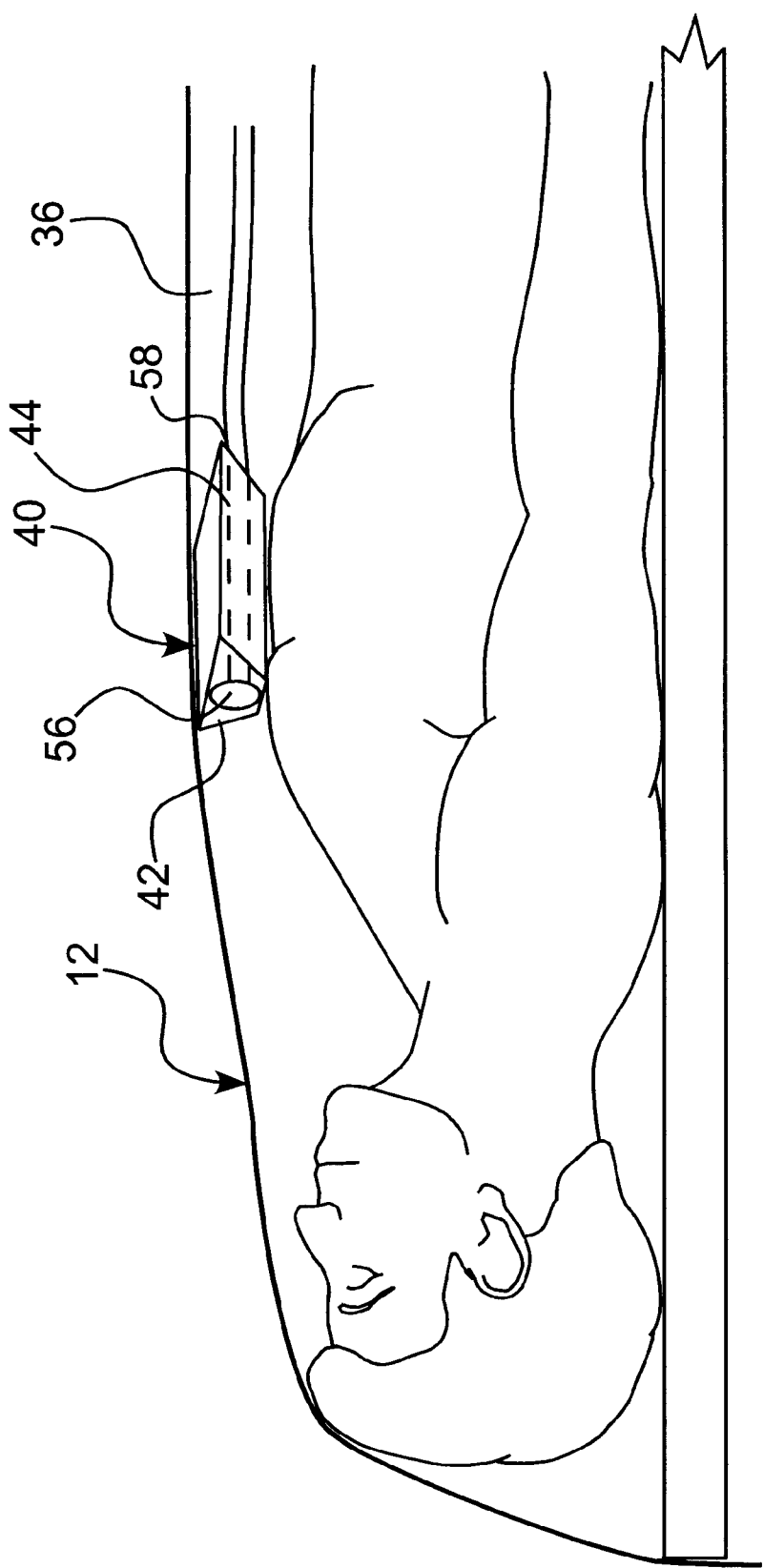
FIG. 4 is a drawing of an embodiment of the present invention placed on a patient.

FIG. 4 illustrates an embodiment of the evacuating surgical drape support 40 of the present invention supporting surgical drape 12. The drape support 40 preferably can have a funnel-shaped passageway 44 with the larger opening 56 of the funnel lying on a front face 42 of the surgical drape support 40 and the smaller opening 58 of the funnel-shaped passageway 44 lying on the rear face 46 of the surgical drape support 40. Suction tubing 36 can be connected to the smaller opening 58 of the funnel-shaped passageway 44 and suction applied to actively evacuate exhaled air containing heat, moisture and $CO_2$ from the space under the surgical drape around the patient's face. When the surgical drape support is used, it is placed upon the patient at about the sternal region and positioned such that the front face 42 is positioned proximal, or closer, to the patient's face and the shorter side of the rear face 46 is positioned distal, or farther, from the patient's face.

As shown in FIG. 5, the evacuating surgical drape support 40 of the present invention preferably has a trapezoidal-shaped top 48 and bottom (not shown). The larger opening 56 of the passageway 44 lies on the front face 42 of the evacuating drape support 40 of the present invention. A tubing connector 50 can preferably be attached to the smaller opening 58 of the funnel-shaped passageway 44 and connected to the operating theater suction tubing.

FIG. 6 shows the front 42 and top 48 faces of an embodiment of the present invention 40. The trapezoidal shape seen in the front 42 and top 48 faces is preferred so that the evacuating surgical drape support 40 will approximate the width of the average person's face at the top of front face 42 of the support with the longer side of the trapezoidal front face being preferably about 13.97 cm (5.5 in.) and the shorter side being preferably about 10.16 cm (4 in.). The streamlined shape of the evacuating surgical drape support of the present invention will provide both a more stable contact with the patient's body and will present a minimal obstruction to the surgeon and other operating room personnel as it sits atop the patient's chest. The support can preferably be about 8.89 cm (3.5 in.) high, so as not to impede the surgeon's access to the patient's face. Because the bottom face is flat, it will allow the drape support 40 to rest more securely on the patient's chest than would a rounded object, such as a bottle. The drape support 40 may preferably be provided with double-sided adhesive tape to secure the support to the patient. Another preferred method of securing the drape support of the present invention to the patient, can be through the use of a Velcro® strip placed on the bottom face of the evacuating drape support with a strip or a patch attached to the patient's surgical garment at about the sternal region. Additionally, because the top face 48 of the evacuating drape support is flat, it may provide an auxiliary area for the operating room personnel to place instruments used during surgery.

FIG. 7 shows the top 48 and rear 46 faces of an embodiment of the present invention, with first and second side faces 54 and smaller opening 58.

The evacuating drape support of the present invention can preferably be made of plastic, such as polypropylene, polyurethane or other synthetic material that is lightweight, inexpensive, disposable and can be sterilized. Even though the shape of the preferred embodiment disclosed herein for the top, bottom, front and rear faces is a trapezoid, other embodiments contemplated by the inventor include utilizing other shapes such as rectangles and squares for the faces. The surgical drape support of the present invention can be hollow or solid. Embodiments contemplated by the inventor in this regard include, but are not limited to, a framework, preferably made of wire, which encompasses an air passageway. The framework can have a top surface sized to support a surgical drape and a bottom surface adapted to be supported by a patient. Further embodiments contemplated by the inventor include a cylindrical-shaped structure with a top sized to support a surgical drape and a bottom adapted to be supported by a patient. This embodiment would have only one side face, through which both openings of the passageway would be located. A version of this embodiment would be a substantially triangular top and bottom faced device, essentially a "slice of pie" of the above-detailed cylindrical embodiment.

The foregoing illustration of the preferred embodiment of the present invention is offered for the purpose of illustration and not limitation. It will be readily apparent to those skilled in the art that the embodiment described herein may be modified or revised in various ways without departing from the spirit and scope of the invention. The scope of the invention is to be measured by the appended claims.

I claim:

1. A surgical drape support comprising:
    a member having a polygonal top face sized to support a surgical drape, a polygonal bottom face adapted to be support by a patient, a polygonal front face, a polygonal rear face and a first and second side face.

2. The surgical drape support of claim 1, wherein said polygonal top face and said polygonal bottom face are trapezoidal-shaped.

3. The surgical drape support of claim 1, wherein said polygonal front face and said polygonal rear face are trapezoidal-shaped.

4. The surgical drape support of claim 1, wherein the shape of said polygonal top face and said polygonal bottom face are selected from the group consisting of squares and rectangles.

5. The surgical drape support of claim 1, wherein the shape of said polygonal front face and said polygonal rear face are selected from the group consisting of squares and rectangles.

6. The surgical drape support of claim 1, wherein said member defines a passageway extending from said polygonal front face to said polygonal rear face.

7. The surgical drape support of claim 6, wherein said passageway is funnel-shaped, with said passageway being oriented such that a larger opening of said funnel-shaped passageway lies on said polygonal front face and a smaller opening of said funnel-shaped passageway lies on said polygonal rear face of said member.

8. The surgical drape support of claim 6 further including a tubing connector attached to said opening in said polygonal rear face.

9. The surgical drape support of claim 1, wherein said in member is hollow.

10. The surgical drape support of claim 1, wherein said member is solid.

11. The surgical drape support of claim 1, wherein said member is made of plastic.

12. The surgical drape support of claim 1, wherein said member is made of polypropylene.

13. The surgical drape support of claim 1, wherein said member is made of polyurethane.

14. The surgical drape support of claim 9, wherein said member is made of a framework.

15. The surgical drape support of claim 1 further including double-sided adhesive tape attached to said polygonal bottom face.

16. The surgical drape support of claim 1 further including at least one hook and loop strip attached to said polygonal bottom face.

17. A method of evacuating the air under a surgical drape, said method comprising:

supporting said surgical drape with a surgical drape support comprising, a member having a polygonal top face sized to support a surgical drape, a polygonal bottom face adapted to be support by a patient, a polygonal front face, a polygonal rear face and a first and second side face, said member defining a passageway extending from said polygonal front face to said polygonal rear face;

attaching tubing to said passageway and to a means for actively evacuating air; and actively evacuating said air from under said surgical drape by operating said means.

18. The method of claim 17, wherein said polygonal top face and said polygonal bottom face are trapezoidal-shaped.

19. The method of claim 17, wherein said polygonal front face and said polygonal rear face are trapezoidal-shaped.

20. The method of claim 17, wherein the shape of said polygonal top face and said polygonal bottom face are selected from the group consisting of squares and rectangles.

21. The method of claim 17, wherein the shape of said polygonal front face and said polygonal rear face are selected from the group consisting of squares and rectangles.

22. The method of claim 17, wherein said passageway is funnel-shaped, with said passageway being oriented such that a larger opening of said funnel-shaped passageway lies on said polygonal front face and a smaller opening of said funnel-shaped passageway lies on said polygonal rear face of said member.

23. The method of claim 17, wherein said member is hollow.

24. The method of claim 17, wherein said member is solid.

25. The method of claim 17, wherein said member is made of plastic.

26. The method of claim 17, wherein said member is made of polypropylene.

27. The method of claim 17, wherein said member is made of polyurethane.

28. The method of claim 17, wherein said member is made of a framework.

29. The method of claim 17 wherein said polygonal bottom face includes double-sided adhesive tape attached thereto.

30. The method of claim 17 wherein said polygonal bottom face includes at least one Velcro® strip attached thereto.

31. A method of reducing patient anxiety during head and neck surgery, said method comprising:

supporting a surgical drape with a surgical drape support comprising, a member having a polygonal top face sized to support a surgical drape, a polygonal bottom face adapted to be support by a patient, a polygonal front face, a polygonal rear face and a first and second side face, said member defining a passageway extending from said polygonal front face to said polygonal rear face;

attaching tubing to said passageway and to a means for actively evacuating air; and actively evacuating said air from under said surgical drape by operating said means thereby reducing patient anxiety.

32. A method of reducing carbon dioxide under a surgical drape during head and neck surgery, said method comprising:

supporting said surgical drape with a surgical drape support comprising, a member having a polygonal top face sized to support a surgical drape, a polygonal bottom face adapted to be support by a patient, a polygonal front face, a polygonal rear face and a first and second side face, said member defining a passageway extending from said polygonal front face to said polygonal rear face;

attaching tubing to said passageway and to a means for actively evacuating air containing carbon dioxide; and reducing the carbon dioxide.

* * * * *

UNITED STATES PATENT AND TRADEMARK OFFICE
CERTIFICATE OF CORRECTION

PATENT NO. : 6,302,109 B1
DATED : October 16, 2001
INVENTOR(S) : Robert E. Parnes It is certified that error appears in the above-identified patent and that said Letters Patent is hereby corrected as shown below:

<u>Title page,</u>
References Cited, the name of the Inventor of U.S. Patent No. 5,730, 153 should read
-- Chang -- and not "Cheng".

<u>Column 2,</u>
Lines 32 and 33, delete "check" and insert in its place -- "cheek" --

<u>Column 7, claim 9,</u>
Delete the word "in" after the word "said" and before the word "member"

Signed and Sealed this

Nineteenth Day of March, 2002

Attest:

*Attesting Officer*

JAMES E. ROGAN
*Director of the United States Patent and Trademark Office*